United States Patent [19]                    [11]  3,930,949
Kutzbach et al.                                    [45]  Jan. 6, 1976

[54] PROCESS FOR THE PRODUCTION OF 7-AMINO-Δ³-CEPHEM DERIVATIVES
[75] Inventors: Carl Kutzbach, Wuppertal; Uwe Petersen, Cologne, both of Germany
[73] Assignee: Bayer Aktiengesellschaft, Germany
[22] Filed: Oct. 22, 1974
[21] Appl. No.: 517,002

[30]     Foreign Application Priority Data
         Nov. 3, 1973   Germany............................ 2355078

[52] U.S. Cl. ............................... 195/29; 195/36 P
[51] Int. Cl.² ......................................... C12D 1/02
[58] Field of Search .......... 195/36 R, 36 P, 29, 36 C

[56]            References Cited
              UNITED STATES PATENTS
3,239,394   3/1966   Walton............................. 195/36 R
3,507,861   4/1970   Morin et al...................... 195/36 P
3,736,230   5/1973   Delin et al....................... 195/36 P

*Primary Examiner*—Alvin E. Tanenholtz

[57]              ABSTRACT
7-Amino-Δ³-cephem derivatives of the formula:

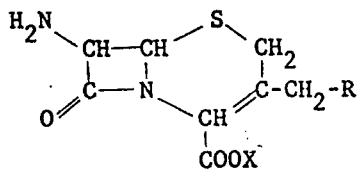

wherein:
R is hydrogen; hydroxy; amino; cyano;

—O—CO—NH₂;

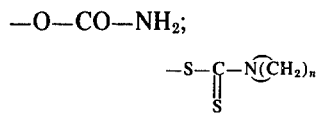

wherein $n$ is an integer from 4 to 6; —O—CO—R¹; —NH—CO—R¹ or —S—CS—O—R¹ wherein R¹ is alkyl of 1 to 4 carbon atoms; -S-Het or Het wherein Het is a 5- or 6-membered hetero-aromatic ring unsubstituted or substituted by 1 to 3 alkyl moieties of 1 to 3 carbon atoms or said ring having a positive charge; and X is hydrogen; or, is a negative charge if R has a positive charge, are obtained by reacting a compound of the formula:

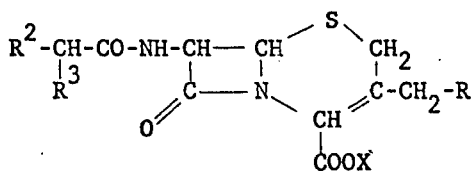

or a salt thereof with an inorganic or organic base, wherein:
  R and X are as above defined;
  R² is phenyl, phenoxy, 2-thienyl or 2-furyl, unsubstituted or substituted in the ring by amino, hydroxy or alkyl of 1 to 3 carbon atoms; and
  R³ is hydrogen, amino, hydroxy or alkyl of 1 to 3 carbon atoms,
with penicillinacylase which is bound by convalent bonds to a water-insoluble carrier.

17 Claims, No Drawings

PROCESS FOR THE PRODUCTION OF 7-AMINO-Δ³-CEPHEM DERIVATIVES

The present invention relates to a new process for the production of certain known 7-amino-Δ³-cephem derivatives which are useful for the synthesis of antimicrobial compounds.

It is known in the art that 7-amino-cephalosporanic acid is obtained by, for example, the splitting of cephalosporin C with cultures of various micro-organisms (see, U.S. Pat. No. 3,239,394) or by chemical splitting in accordance with various methods (see, German Auslegeschrift No. 1,176,147, German Offenlegungsschrift No. 1,145,615 and U.S. Pat. No. 3,272,809). Desacetoxy-cephalosporin C can, after catalytic reduction (see, U.S. Pat. No. 3,124,576), be converted analogously into 7-amino-desacetoxy-cephalosporanic acid. German Offenlegungsschrift No. 2,212,276 has also disclosed a process for the enzymatic splitting of 7-phenoxyacetamidodesacetoxy-cephalosporanic acid to 7-amino-desacetoxy-cephalosporanic acid with the aid of an adsorptively bound enzyme from *Bacillus megaterium* B 400. Several processes for splitting penicillins with the aid of penicillinacylase bound by covalent bonds to water-insoluble carriers have also been disclosed (see, German Offenlegungsschrifts Nos. 1,907,365, 1,917,057 and 2,215,687).

More particularly, the present invention is concerned with a process for the production of 7-amino-Δ³-cephem derivatives of the formula:

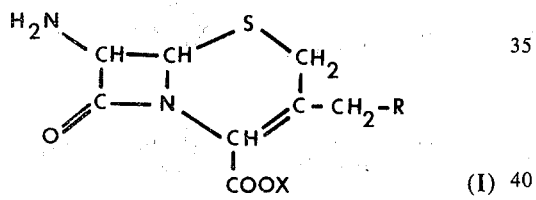
(I)

wherein
R is hydrogen; hydroxy; amino; cyano; —O—CO—NH₂;

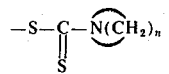

wherein $n$ is an integer from 4 to 6;
—O—CO—R¹, —NH—CO—R¹ or —S—CS—O—R¹ wherein R¹ is alkyl of 1 to 4 carbon atoms; or
-S-Het or Het wherein Het is a 5- or 6-membered hetero-aromatic ring or said ring having a positive charge; and
X is hydrogen; or, is a negative charge if radical R has a positive charge,
which comprises reacting a compound of the formula:

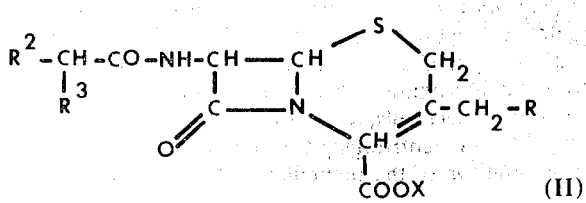
(II)

or a salt thereof with an inorganic or organic base, wherein:
R and X are as above defined,
R² is phenyl, phenoxy, 2-thienyl or 2-furyl, unsubstituted or substituted in the ring by amino, hydroxy or alkyl of 1 to 3 carbon atoms; and
R³ is hydrogen, amino, hydroxy or alkyl of 1 to 3 carbon atoms,
with penicillinacylase which is bound by covalent bonds to a water-insoluble carrier.

The resulting 7-amino-Δ³-cephem derivatives of the formula (I) are then isolated.

According to one embodiment of the present invention:
R¹ is alkyl of 1 or 2 carbon atoms;
$n$ is 4 or 5;
said hetero-aromatic ring contains from 1 to 3 of the same or different hetero-atoms selected from the group consisting of oxygen, sulfur and nitrogen, the alkyl substituent on said hetero-aromatic ring is of 1 or 2 carbon atoms and the alkyl substituent on the phenyl, phenoxy, 2-thienyl or 2-furyl substituent is of 1 or 2 carbon atoms.

According to another embodiment of the present invention:
R, R³ and X are each hydrogen; and
R² is phenyl or phenoxy; or
R is —O—CO—CH₃;
R³ and X are each hydrogen; and
R² is phenyl or phenoxy.

According to another embodiment of the present invention:
R is hydrogen, —O—CO—CH₃; or

R² is phenyl, phenoxy or thienyl;
R³ is hydrogen or amino; and
X is hydrogen or a negative charge.

According to another embodiment of the present invention:
R is hydrogen or —O—CO—CH₃;
R² is phenyl or phenoxy;
R³ is hydrogen; and
X is hydrogen.

According to another embodiment of the present invention:
R is hydrogen, —O—CO—CH₃; or

R² is phenyl, phenoxy or thienyl;
R³ is hydrogen or amino; and
X is hydrogen or a negative charge.

Examples of salts of the compounds of the formulae (I) and (II) include the alkali metal salts, such as sodium and potassium salts, alkaline earth metal salts, such as calcium salts, ammonium salts and salts formed with aliphatic, araliphatic or aromatic amines. The primary, secondary and tertiary alkylamines of 1 to 4 carbon atoms in the alkyl moiety and in which the alkyl moieties can be substituted by hydroxy moieties, for example, ethylamine, triethylamine and hydroxyethylamine, and cyclic amines, for example, pyridine, piperidine, morpholine, piperazine and N-methylpiperazine.

Surprisingly, penicillinacylase which is carrier-bound as described above (hereinafter called "carrier-bound penicillinacylase") splits the compounds of the formula (II) at practically the same speed as corresponding penicillins.

The process of the invention has a number of advantages over the known processes for the preparation of the compounds of the formula (I). For example, while enzymes for cell cultures can only be used once, it is possible to use the carrier-bound penicillinacylase repeatedly. Furthermore, the process according to the invention can give the compounds of the formula (I) in very good purity and high yields, with very little technical effort. Compared to the use of an enzyme which is merely bound adsorptively, in accordance with German Offenlegungsschrift No. 2,212,276, the use, according to the invention, of the penicillinacylase bound by covalent bonds has the advantage that the enzyme remains firmly bound even when high concentrations of the cephalosporin substrate of the formula (II) are used, so that the process according to the invention is substantially more economical.

If, for example, 7-phenyl-acetamido-desacetoxy-cephalosporanic acid is used as the starting compound of formula (II), the course of the reaction according to the invention can be represented by the following formula scheme:

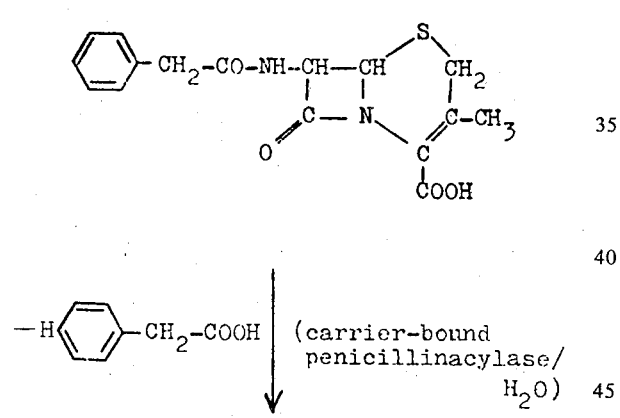

Compounds of formula (II) are already known and can be obtained in accordance with known processes (see, for example, E. H. Flynn, *Cephalosporins and Penicillins, Chemistry and Biology*, Academic Press, New York, 1972).

The compounds set forth in the table below are representative of the starting compounds of the formula (II):

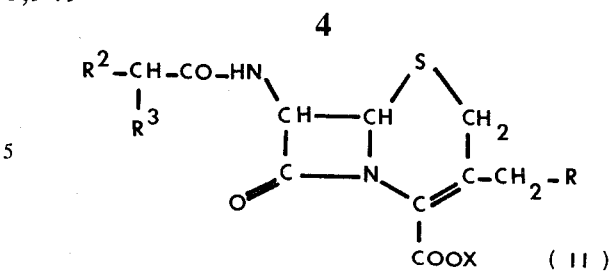

| | R | $R^2$ | $R^3$ | X |
|---|---|---|---|---|
| (a) | —OCOCH₃ | thienyl | H | H |
| (b) | —N⊕(pyridinium) | thienyl | H | — |
| (c) | H | phenyl | NH₂ | H |
| (d) | H | phenyl | H | H |
| (e) | H | phenyl-O— | H | H |
| (f) | —O—CO—CH₃ | phenyl-O— | H | H |
| (g) | —O—CO—CH₃ | phenyl | H | H |
| (h) | —O—CO—CH₃ | phenyl | NH₂ | H |

Compounds (d), (e), (f) and (g) are very particularly preferred for use in the present process.

Penicillinacylase of the most diverse origin, bound by covalent bonds to a water-insoluble carrier can be used in the present process.

Penicillinacylase (Enzyme Commission 3.5.1.11) can be obtained from numerous micro-organisms in accordance with generally known methods (see, German Offenlegungsschriften Nos. 1,907,365 and 2,217,745), for example from bacteria, especially *Escherichia coli*, Erwinia or Actinomycetes, such as Streptomyces, Micromonospora or Norcardia or fungi, such as Fusarium and yeasts. Penicillinacylase from *Escherichia coli*, for example from a strain of *Escherichia coli* which has been deposited under ATCC 11,105, is particularly preferred. The isolation of penicillinacylase from *Escherichia coli* is effected, for example, according to German Offenlegungsschrift No. 2,217,745, by adjusting a crude extract of *Escherichia coli* cells, which in addition to penicillinacylase also contains cell fragments of the *Escherichia coli* cells, to a pH value of 3.5 to 5.5, preferably 5.0, and centrifuging the extract, then treating the clear solution of the penicillinacylase, obtained as the supernatant liquid, with aluminium silicate, preferably bentonite, separating off the adsorbate, for example in any known manner, and eluting, for example, with an 0.1–1.0 molar solution of sodium acetate or potassium acetate at about pH 8.5.

The enriched clear solution of the penicillinacylase thereby obtained can optionally be purified further chromatographically on macroporous ion exchangers, for example, sulphoethyl-cellulose.

The carrier-bound penicillinacylase may for example be practically any enzyme resin in which penicillinacylase is bound by covalent bonds to a water-insoluble carrier polymer. Many such enzyme resins are already known or obtainable in accordance with known methods (see, for example, German Offenlegungsschriften Nos. 1,907,365, 1,917,057, 2,157,972, 2,215,539, 2,215,687 and 2,008,996; E. Katchalski, *Biochemistry*, 3 (1964), pages 1,905–1,919; and H. D. Orth and W. Brümmer, *Angewandte Chemie* 84 (1972), pages 319–368). Examples of suitable enzyme resins are those in which the penicillinacylase is bound by covalent bonds, by means of cyanogen bromide, to polysaccharides such as dextran or crosslinked agarose (see German Offenlegungsschrift No. 1,907,365). It is also possible to use enzyme resins which are prepared by reacting penicillinacylase with bromoacetylcellulose, or which are prepared by reacting penicillinacylase with an ion exchanger substance based on three-dimensionally crosslinked dextran, substituted by carboxyl groups, in the presence of a compound capable of amide formation, for example a carbodiimide, and activated ion exchange resins such as the acid chloride of an acrylic acid resin, and resins of ethylene and maleic anhydride crosslinked with hydrazine, can also be employed. (See, German Offenlegungsschrift No. 1,917,057). An enzyme resin in which, according to German Offenlegungsschrift No. 2,157,972, penicillinacylase is bound by covalent bonds to a copolymer of acrylamide, N,N'-methylene-bis-acrylamide and maleic acid is also very suitable. The enzyme resin can for example be obtained as follows. An appropriate copolymer is prepared in accordance with methods which are in themselves known. After the copolymerization, the gel-like resin is forced through a sieve of 0.5 mm mesh width and is washed well and dried in vacuo. The copolymerized dicarboxylic acid is converted to the dicarboxylic acid anhydride by heating to 180°C for 2 hours. Preferably, at least 10 g of copolymer are employed per g of enzyme. About 3–4 g of the copolymer are added to the solution of the enzyme in 250 ml of 0.05 M phosphate buffer of pH 5.5, the mixture is stirred intensively and after 2 hours the remaining copolymer is added in small portions. During the entire period of reaction the pH value is kept constant by adding dilute sodium hydroxide solution. If, after 5 hours, the aqueous supernatant liquid still contains unconverted enzyme, further copolymer is added. A ratio of 1 part of enzyme to 15–20 parts of copolymer generally suffices for complete conversion. After the coupling, the carrier-bound penicillinacylase is filtered off and washed thoroughly with water and 1 M sodium chloride solution.

Particularly preferred enzyme resins usable according to the present invention are those which are described in German Offenlegungsschrift No. 2,215,539 and in which the penicillinacylase is bound to crosslinked copolymers which consist of copolymeric units of the following composition:

A. 0.1 to 50, preferably 2 to 20, % by weight of $\alpha,\beta$-mono-olefinically unsaturated dicarboxylic anhydrides of 4 to 9, preferably 4 or 5, carbon atoms, for example maleic anhydride, itaconic anhydride and citraconic anhydride, especially maleic anhydride, and B. 99.9 to 50, preferably 80 to 98, % by weight of di- and/or poly-(meth)acrylates of diols and/or polyols, preferably diacrylates or dimethacrylates of diols with 2 to 4 carbon atoms and/or reaction products of 1 mol of these diols with 1 to 20 mols of alkylene oxide having 2 to 4 carbon atoms or trimethylolpropane trimethacrylate, especially the dimethacrylates of ethylene glycol, diethylene glycol, triethylene glycol, tetraethylene glycol or higher polyalkylenglycols with molecular weights of up to 1,000, or their mixtures.

The polymerization is carried out by the precipitation polymerization or bead polymerization methods in solvents or solvent mixtures which are inert towards anhydride groups, for example, benzene, at temperatures of 20°–200°C, for example, at 60°–70°C, in the presence of radical-forming compounds, for example, azoisobutyric acid dinitrile. To prepare the enzyme resins, the copolymers thus obtained are introduced into an aqueous solution of the penicillinacylase while a pH of 5.7 to 6.8 is maintained, for example, at from 4 to approximately 30°C (and using, for example, 1 part by weight of penicillinacylase per 10–50 parts by weight of polymeric carrier). After approximately 2 hours, the product is filtered off or centrifuged and the residue is washed with salt solutions of high ionic strength, for example, a 1 molar aqueous sodium chloride solution.

Further particularly preferred enzyme resins which can be used according to the invention are those which are described in German Offenlegungsschrift No. 2,215,687 and in which penicillinacylase is bound to copolymers which consist of crosslinked copolymers of the following copolymerized units:

A. 0.1 to 30, preferably 2 to 20, % by weight of $\alpha,\beta$-mono-olefinically unsaturated dicarboxylic acid anhydrides of 4 to 9, preferably 4 or 5, carbon atoms, such as maleic anhydride, itaconic anhydride and citraconic anhydride, preferably maleic anhydride;

B. 35 to 90, preferably 50 to 85, % by weight of di and/or poly-(meth)acrylates of diols and/or polyols, such as diacrylates or dimethacrylates of diols with 2 to 4 carbon atoms and/or reaction products of one mol of these diols with 1 to 10 mols of alkylene oxide with 2 to 4 carbon atoms, or trimethylolpropane trimethacrylate, for example, dimethylacrylates of ethylene glycol, diethylene glycol, triethylene glycol, tetraethylene glycol or higher polyalkylglycols with molecular weights of up to 500, or their mixtures; and C. 5 to 60, preferably 10 to 50, % by weight of at least one hydrophilic monomer not mentioned under (B), preferably a singly unsaturated hydrophilic monomer which contains at least one carboxyl, aminocarbonyl, sulpho or sulphamoyl group, the amino groups of the aminocarbonyl or sulphamoyl radical optionally being substituted by alkyl groups with 1 to 4 carbon atoms or by alkoxymethyl with 1 to 4 carbon atoms in the alkyl moiety. Examples which may be mentioned are acrylic acid, methacrylic acid, maleic acid half-esters with 1 to 8 carbon atoms in the alcohol radical, N-vinyllactams such as N-vinylpyrrolidone, methacrylamide, N-substituted (meth)acrylamides, such as N-methyl- and N-methoxymethyl-(meth)acrylamide, and N-acroloyl-dimethyltaurine.

The sum of the constituents (A) to (C) is 100% by weight. The crosslinked copolymers have bulk volumes of 2–20 ml/g and specific surface areas of 1 to 400 m²/g and contain, after the hydrolysis of the anhydride groups, from 0.02 to 11 milliequivalents of acid per gram.

The polymerization may be carried out by the precipitation polymerization or bead polymerization method, in solvents or solvent mixtures which are inert towards anhydride groups, for example benzene, at temperatures from 20° to 200°, preferably 50° to 100°C, for example at 60° to 70°C, in the presence of radical-forming compounds, for example azoisobutyric acid dinitrile. To prepare the enzyme resin, the polymer may be introduced into an aqueous solution of the penicillinacylase (preferably 1 part by weight of penicillinacylase to 10 to 50 parts by weight of resin) at temperatures from 0° to 30°C, for example from 4° to 20°C, while keeping the pH value at 5.7 to 6.8 by addition of a base, for example by means of sodium hydroxide solution. After completion of the reaction, the product may be filtered off and washed with a buffer solution or a salt solution, for example a 1 molar sodium chloride solution.

An enzyme resin in which the penicillinacylase is bound by covalent bonds to a copolymer of tetraethylene glycol dimethacrylate, maleic anhydride and, optionally, methacrylic acid, is very particularly preferred for use.

The reaction according to the invention, for splitting the compounds of the formula (II) to give those of the formula (I), may be carried out in a diluent. The diluent may be water or a mixture of water and up to 10% of an organic solvent, preferably methanol, ethanol, acetone or dimethylformamide.

The reaction is generally carried out at 20° to 45°C, preferably 35° to 40°C.

In carrying out the process according to the invention, the compound of the formula (II) may be dissolved in the diluent described above, preferably water; preferably, the solution should contain 2 to 20, and especially 4 to 6, % by weight of the compounds of the formula (II). The solution is brought into contact in any desired manner with the enzyme resin. For example, the enzyme resin can be suspended in the solution.

For neutralising the acyl radical split off during the reaction, constant monitoring and adjustment of the pH value is very desirable. During the reaction, the pH should preferably be kept at 6 to 9, in particular 7.5 to 8.5. This can be done, if necessary, by adding a suitable base to the reaction mixture. An inorganic or organic base can be used for this purpose, such as sodium phosphate, alkali metal hydroxides, alkali metal carbonates and bicarbonates, ammonia, primary, secondary and tertiary aliphatic and aromatic amines and heterocyclic bases. Examples which may be mentioned are sodium hydroxide and potassium hydroxide, sodium carbonate and potassium carbonate, sodium bicarbonate and potassium bicarbonate, ethylamine, methylethylamine, triethylamine, mono-, di- and tri-hydroxyethylamine, aniline, pyridine and piperidine. The consumption of base indicates both the rate of reaction and the completion of the reaction.

The rate of reaction depends above all on the ratio of the amount of available carrier-bound penicillinacylase to the amount of the compound of the formula (II) which is employed, and on the specific activity of the carrier-bound penicillinacylase which is employed. The specific activity of the carrier-bound penicillinacylase is quoted in units/g of moist weight. 1 Unit is defined as the penicillinacylase activity which in one minute hydrolyzes one micromol of penicillin G to 6-aminopenicillanic acid and phenylacetic acid at 37°C and pH 7.8.

The splitting of 1 kg of 7-phenylacetamido-desacetoxycephalosporanic acid within 2 hours requires about 70,000 units of carrier-bound penicillinacylase, corresponding to about 1 kg of moist enzyme resin. At a concentration of 6%, the reaction volume is 16.6 l. If longer splitting times are allowed, correspondingly less carrier-bound penicillinacylase is required.

After completion of the splitting reaction, the penicillinacylase may be separated off, for example by filtration or centrifuging, and can immediately be employed for a further splitting batch.

The compound of the formula (I) which is formed may be isolated from the clear solution, and this may be done in accordance with generally customary procedures. Examples of customary procedures are precipitation with inorganic mineral acids, such as hydrochloric acid, sulphuric acid or phosphoric acid, or with organic carboxylic acids, such as acetic acid, at the isoelectric point, and chromatographic procedures. The precipitated product, or product obtained by chromatography, may be washed with a suitable solvent, for example butyl acetate or acetone, in order completely to remove the radical which has been split off, and may be dried in vacuo. This may yield the substantially pure compound of the formula (I).

The compounds of the formula (I) obtainable according to the invention can be converted into compounds having antimicrobial activity in accordance with methods per se known, for example by acylation at the 7-position amino group (see, for example, E. H. Flynn, *Cephalosporins and Penicillins, Chemistry and Biology*, Academic Press, New York, 1972).

Examples 1–5 below illustrate the process according to the invention; Examples A and C illustrate the preparation of a carrier-bound penicillinacylase, and Example B illustrates the preparation of a penicillinacylase for making a carrier-bound penicillinacylase.

EXAMPLE 1

2 Mmol of the compound of the formula (II) which was to be split were dissolved in 20 ml of water (optionally with addition of sodium hydroxide solution) at pH 7.5. About 5 g (moist weight) of the enzyme resin (prepared as in Example A) were added to the solution which was stirred in a vessel thermostatically controlled at 37°C. During the reaction, the pH value was kept constant at pH 7.5 by addition of M/10 NaOH by means of a pH-stat. The termination of the addition of NaOH indicated the end of the reaction. After completion of the reaction, the carrier-bound penicillinacylase was filtered off on a glass frit and was rinsed with water. The filtrate and wash water were concentrated to 5 ml in vacuo at 30°C. The concentrated solution was mixed with 5 ml of butyl acetate and the cephalosporanic acid was precipitated by adding 5 N HCl until the isoelectric point of 3.7 was reached. After the sample had stood in a refrigerator for 2–3 hours, the crystalline product was filtered off, washed with 10 ml of water and 10 ml of acetone, and dried in vacuo.

The strength of the products was determined by photometric determination of the liberated 7-amino group after reaction with p-dimethylaminobenzaldehyde, in a modification of the method of Svotek (Czech. Pat. No. 116,959 (1965)).

The extinction at 415 nm was compared with standard curves for pure 7-aminocephalosporanic acid and 7-aminodesacetoxy-cephalosporanic acid.

In addition, the identity of the products was proved by infrared spectra and $^1$H nuclear resonance spectra and by paper chromatography in a butanol:glacial acetic acid:water system (12:3:5).

The following reactions were carried out in this manner:

EXAMPLE 1 a

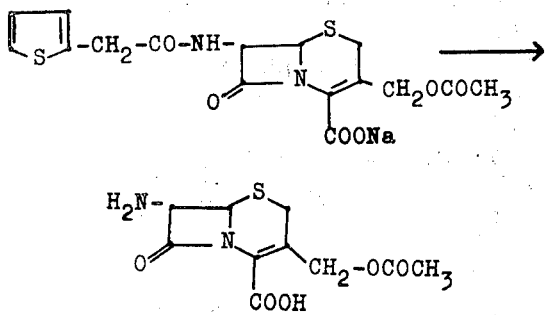

Starting compound:

908 mg of 7-(2-thienyl)-acetamido-cephalosporanic acid (sodium salt). Duration of reaction: 42 minutes End product: 7-aminocephalosporanic acid. Yield: 520 mg (88% of theory), purity: 98%. Rf: 0.27 (no desacetyl-7-aminocephalosporanic acid with Rf 0.10).

EXAMPLE 1 b

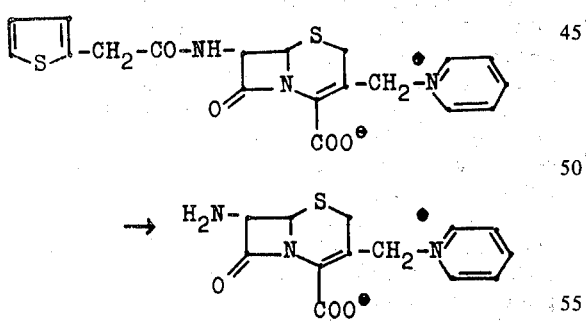

Starting compound:

866 mg of 7-(2-thienyl)-acetamido-3-pyridinium-methyl-Δ³-cephem-4-carboxylate End product: 7-amino-3-pyridiniummethyl-Δ³-cephem-4-carboxylate. Reaction time: 35 minutes. Rf: 0.05.

Because of the pyridine ring in the molecule, the product of this reaction could not be isolated by precipitation at the isoelectric point. The completeness of reaction and identity of the product were demonstrated by paper chromatography.

EXAMPLE 1 c

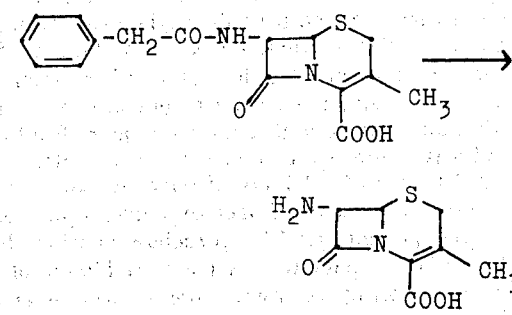

Starting compound:

687 Mg of 7-phenylacetamido-desacetoxycephalosporanic acid.

Duration of reaction: 27 minutes. End product: 7-amino-desacetoxy-cephalosporanic acid. Yield: 350 mg (84% of theory), purity: 99%. Melting point: 238°–240°C (decomposition).

EXAMPLE 1 d

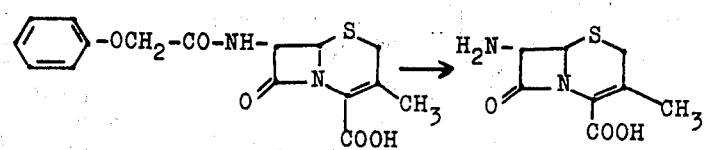

Starting compound: 696 mg of 7-phenoxyacetamido-desacetoxycephalosporanic acid. End product: 7-amino-desacetoxy-cephalosporanic acid. Yield: 350 mg (82% of theory), purity: 96%. Melting point: 238°–240°C (decomposition).

EXAMPLE 1 e

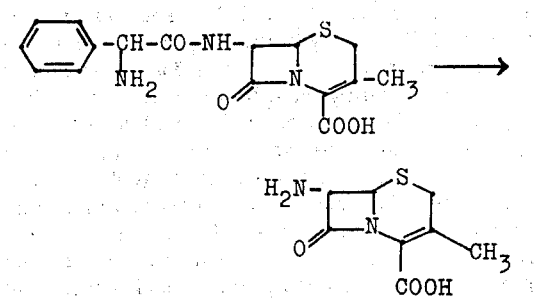

Starting compound:

696 Mg of 7-(α-amino-phenylacetyl)-desacetoxycephalosporanic acid. End product: 7-aminodesacetoxycephalosporanic acid. Yield: 364 mg (85% of theory), purity: 98%.

EXAMPLE 2

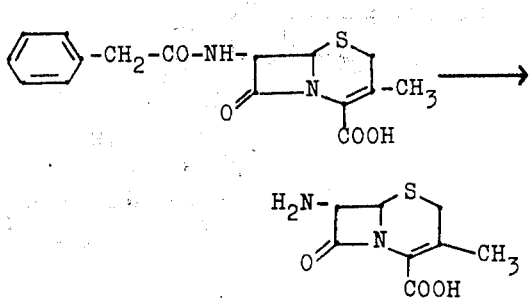

1 Kg of 7-phenylacetamido-desacetoxycephalosporanic acid was dissolved in 12.5 liters of water and split completely over the course of 2 hours at 38°C by adding 1 kg of carrier-bound penicillinacylase (according to Example A). The pH value was kept constant at 7.5 by continuous addition of triethylamine. After completion of the reaction, the carrier-bound enzyme was filtered off and washed with 2 liters of water. The filtrate and wash water were concentrated to 3 liters in vacuo at 30° to 40°C. 2 liters of butyl acetate were added and the 7-amino-desacetoxycephalosporanic acid was precipitated with 5 N hydrochloric acid at pH 3.7 ± 0.1. After 2 hours, the crystals were filtered off, washed with 1 liter of water and 1 liter of acetone and dried in vacuo at 40°C.

Yield: 574 g (89% of theory); purity: 98%.

The same carrier-bound penicillinacylase was used 25 times in succession in the same manner.

The yield from the 25 splitting reactions averaged 90.3% of theory.

EXAMPLE 3

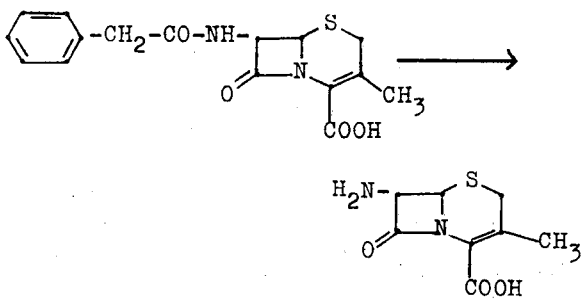

2 G of 7-phenylacetamido-desacetoxycephalosporanic acid (6 mmols) were suspended in 190 ml of water and dissolved by adding 1 N potassium hydroxide solution until the pH value was 7.8. The mixture was warmed to 37°C and 3.2 g of the enzyme resin prepared according to Example A were added. The pH value was kept at 7.8 ± 0.3 during the splitting reaction by adding triethylamine. The reaction was complete after 1½ hours. The enzyme resin was filtered off and washed with water, and the filtrate was concentrated to a quarter of its volume in vacuo at 50°C. After adding 160 ml of methyl isobutyl ketone, the pH of the mixture was adjusted to 4.3 with dilute hydrochloric acid and the 7-amino-desacetoxycephalosporanic acid which had crystallized out was filtered off after standing for 1 hour and was washed with a little water/methyl isobutyl ketone.

Yield: 1.01 g (78.8% of theory). Melting point: 238°–240°C (decomposition).

EXAMPLE 4

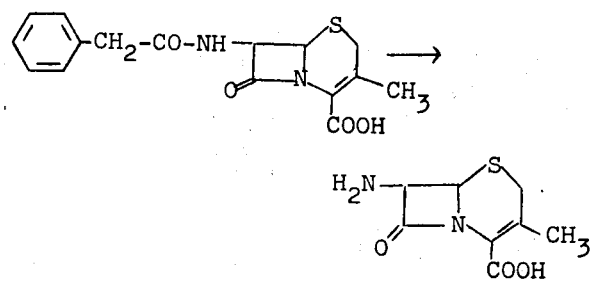

500 g of 7-phenylacetamido-desacetoxycephalosporanic acid were dissolved in 8.3 liters of water and split completely over the course of 4 hours at 38°C, by addition of 220 g of carrier-bound penicillinacylase (according to Example C), analogously to Example 2; the 7-amino-desacetoxycephalosporanic acid formed was precipitated and dried.

Yield: 294 g (91% of theory); purity 97%.

25 splitting reactions were carried out in the same manner with the same carrier-bound penicillinacylase. The average yield from 25 splitting reactions was 90.5%.

EXAMPLE 5

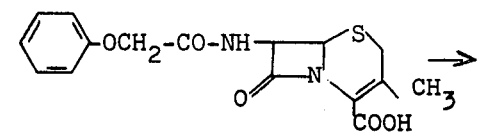

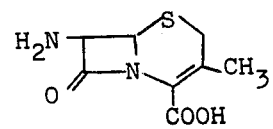

500 g of 7-phenoxyacetamido-desacetoxycephalosporanic acid were dissolved in 8.3 liters of water and reacted with 1.1 kg of carrier-bound penicillinacylase (according to Example C) at 38°C until the splitting was complete. After the uptake of triethylamine had ceased, the mixture was worked up as in Example 2.

Yield: 265 g of 7-amino-desacetoxycephalosporanic acid (86% of theory); purity 98%.

EXAMPLE A 80 g of tetraethylene glycol dimethacrylate, 20 g of maleic anhydride and 1 g of azoisobutyric acid dinitrile were dissolved in 1 liter of benzene and the solution was warmed to 60°C for 4 hours, while stirring. 1 g of azoisobutyric acid dinitrile and 200 ml of petroleum ether (boiling point 100°–140°C) were then added and the mixture was polymerised for a further 5 hours at 70°C. The pulverulent product was filtered off, suspended once in benzene and three times in petroleum ether (boiling point 30°–50°C) and dried in vacuo.

Yield: 94 g. Bulk volume: 3.5 ml/g. Swelling volume in water: 4.7 ml/g. Specific surface area: 5 m²/g. Acid content after saponification of the anhydride groups: 3.5 milliequivalents/g.

100 G of the carrier resin thus prepared were suspended in 3.5 liters of an aqueous solution of 48,000 units of penicillinacylase (specific activity 12 U/mg of protein (biuret test)). The pH value was kept constant at 6.3 by addition of 1 N sodium hydroxide solution while stirring the suspension for 20 hours at 25°C. The resin was then filtered off on a large glass frit and washed with 5 liters of 0.05 M phosphate buffer of pH 7.5, containing 1 M sodium chloride, and subsequently with 5 liters of the same buffer without sodium chloride.

Product: 500 g of moist enzyme resin of specific activity 58 U/g, representing 29,000 units of carrier-bound penicillinacylase ≙ 60% of theory.

EXAMPLE B a. A crude extract which contained penicillinacylase was obtained by culturing *Escherichia coli* in accordance with the process described in German Patent No. 1,111,778, concentrating the culture to a sludge by centrifuging and breaking open the cells in accordance with known mechanical processes, with addition of 3% of methyl isobutyl ketone.

b. 610 Liters of a crude extract thus obtained, containing $5.2 \times 10^6$ U, were diluted to 2,100 liters with deionised water, adjusted to pH 5.0 with sulphuric acid and centrifuged. The clear supernatant liquid contained $5.7 \times 10^6$ U of specific activity 1.7 U/mg. 13.8 kg of bentonite (type B II, Messrs. Erbsloh) were stirred in while readjusting the pH to 5.0, and after 30 minutes the bentonite was separated off in a continuous-flow centrifuge; it was then eluted with 90 liters of 0.5 M sodium acetate solution of pH 8.0, and filtered off. 92.5 liters, containing $4.5 \times 10^6$ U (86% of theory) and having a specific penicillinacylase activity of 6.5 U/mg, were obtained.

EXAMPLE C

60 G of tetraethylene glycol dimethacrylate, 30 g of methacrylic acid, 10 g of maleic anhydride and 1 g of azoisobutyric acid dinitrile were dissolved in 300 ml of acetonitrile. This solution was suspended in 1 liter of benzine (boiling point 100°–140°C) which contained 5 g of a mixture of glycerol mono-oleate and glycerol dioleate and polymerization was carried out for 22 hours at 60°C.

The polymer beads were filtered off, suspended three times in benzene and twice in petroleum ether (boiling point 30°–50°C) and dried in vacuo.

Yield: 94 g. Bulk volume: 44 ml/g. Swelling volume in water: 5.5 ml/g. Specific surface area: 6.6 m²/g. Acid content after saponification of the anhydride groups: 4.3 milliequivalents/g.

100 g of the polymer thus prepared were reacted with 51,000 units of penicillinacylase (specific activity 4.5 U/mg of protein), as in Example A.

Product: 480 g of moist enzyme resin of specific activity 69 U/g, representing 33,000 units of carrier-bound penicillinacylase ≙ 65% of theory.

What is claimed is:

1. A process for the production of a compound of the formula:

[structural formula showing β-lactam with $H_2N$–CH–CH–S–CH$_2$ ring system, COOX group, and =C–CH$_2$–R]

wherein:
R is hydrogen; hydroxy; amino; cyano; —O—CO—NH$_2$;

$$-S-\underset{\underset{S}{\|}}{C}-N(CH_2)_n$$

wherein n is an integer from 4 to 6; —O—CO—R$^1$; —NH—CO—R$^1$ or —S—CS—O—R$^1$ wherein R$^1$ is alkyl of 1 to 4 carbon atoms; -S-Het or Het wherein Het is a 5- or 6-membered hetero-aromatic ring unsubstituted or substituted by 1 to 3 alkyl moieties of 1 to 3 carbon atoms or said ring having a positive charge; and
X is hydrogen; or, is a negative charge if R has a positive charge,
which comprises reacting a compound of the formula:

[structural formula showing $R^2$–CH(R$^3$)–CO–NH–CH–CH–S–CH$_2$ β-lactam ring with COOX and =C–CH$_2$–R]

or a salt thereof with an inorganic or organic base, wherein:
R and X are as above defined;
R$^2$ is phenyl, phenoxy, 2-thienyl or 2-furyl, unsubstituted or substituted in the ring by amino, hydroxy or alkyl of 1 to 3 carbon atoms; and
R$^3$ is hydrogen, amino, hydroxy or alkyl of 1 to 3 carbon atoms,
with penicillinacylase which is bound by covalent bonds to a water-insoluble carrier.

2. A process according to claim 1 wherein
R$^1$ is alkyl of 1 or 2 carbon atoms;
n is 4 or 5;
said hetero-aromatic ring contains from 1 to 3 of the same or different hetero-atoms selected from the group consisting of oxygen, sulfur and nitrogen, the alkyl substituent on said hetero-aromatic ring is of 1 or 2 carbon atoms and the alkyl substituent on the phenyl, phenoxy, 2-thienyl or 2-furyl substituent is of 1 or 2 carbon atoms.

3. A process according to claim 1 wherein
R, R$^3$ and X are each hydrogen; and
R$^2$ is phenyl or phenoxy; or
R is —O—CO—CH$_3$;
R$^3$ and X are each hydrogen; and
R$^2$ is phenyl or phenoxy.

4. A process according to claim 1 wherein
R is hydrogen, —O—CO—CH$_3$; or

[pyridinium cation structure];

R$^2$ is phenyl, phenoxy or thienyl;
R$^3$ is hydrogen or amino; and
X is hydrogen or a negative charge.

5. A process according to claim 1 wherein
R is hydrogen or —O—CO—CH$_3$;
R$^2$ is phenyl or phenoxy;
R$^3$ is hydrogen; and
X is hydrogen.

6. A process according to claim 1 wherein
R is hydrogen, —O—CO—CH$_3$, or

[pyridinium cation structure];

R$^2$ is phenyl, phenoxy or thienyl;
R$^3$ is hydrogen or amino; and
X is hydrogen or a negative charge.

7. A process according to claim 1 wherein the penicillinacylase is bound to cross-linked polymers which consist essentially of copolymeric units comprising:
   a. 0.1 to 50% by weight of α-β-mono-olefinically unsaturated dicarboxylic anhydrides of 4 to 9 carbon atoms; and
   b. 99.9 to 50% by weight of at least one member selected from the group consisting of diacrylates, polyacrylates, dimethacrylates and polymethacrylates.

8. A process according to claim 7 wherein the penicillinacylase is bound to copolymers which consist essentially of cross-linked polymers wherein the copolymerized units comprise:
   a. 0.1 to 30% by weight of α-β-mono-olefinically unsaturated dicarboxylic acid anhydrides of 4 to 9 carbon atoms;
   b. 35 to 90% by weight of at least one member selected from the group consisting of diacrylates, polyacrylates, dimethacrylates and polyacrylates; and
   c. 5 to 60% by weight of at least one hydrophilic monomer other than those set forth in (b) above.

9. A process according to claim 1 wherein the penicillinacylase is obtained from *E. coli*.

10. A process according to claim 9 wherein the *E. coli* is ATCC 11,105.

11. A process according to claim 1 for the production of 7-aminocephalosporanic acid which comprises reacting the sodium salt of 7-(2-thienyl)-acetamido-cephalosporanic acid with penicillinacylase obtained from *E. coli* bound by covalent bonds to a water-insoluble carrier comprising tetraethylene glycol dimethacrylate and maleic anhydride.

12. A process according to claim 1 for the production of 7-amino-3-pyridiniummethyl-Δ$^3$-cephem-4-carboxylate which comprises reacting 7-(2-thienyl)-acetamido-3-pyridiniummethyl-Δ$^3$-cephem-4-carboxylate with penicillinacylase obtained from *E. coli* bound by covalent bonds to a water-insoluble carrier comprising tetraethylene glycol dimethacrylate and maleic anhydride.

13. A process according to claim 1 for the production of 7-amino-desacetoxy-cephalosporanic acid which comprises reacting 7-phenylacetamido-desacetoxy-cephalosporanic acid with penicillinacylase obtained from *E. coli* bound by covalent bonds to a water-insoluble carrier comprising tetraethylene glycol dimethacrylate and maleic anhydride.

14. A process according to claim 1 for the production of 7-amino-desacetoxy-cephalosporanic acid which comprises reacting 7-phenoxyacetamido-desacetoxy-cephalosporanic acid with penicillinacylase obtained from *E. coli* bound by covalent bonds to a water-insoluble carrier comprising tetraethylene glycol dimethacrylate and maleic anhydride.

15. A process according to claim 1 for the production of 7-amino-desacetoxy-cephalosporanic acid which comprises reacting 7-(α-amino-phenylacetyl)-desacetoxy-cephalosporanic acid with penicillinacylase obtained from *E. coli* bound by covalent bonds to a water-insoluble carrier comprising tetraethylene glycol dimethacrylate and maleic anhydride.

16. A process according to claim 1 for the production of 7-amino-desacetoxy-cephalosporanic acid which comprises reacting 7-phenylacetamido-desacetoxy-cephalosporanic acid with penicillinacylase obtained from *E. coli* bound by covalent bonds to a water-insoluble carrier which comprises tetramethylene glycol dimethacrylate, methacrylic acid and maleic anhydride.

17. A process according to claim 1 for the production of 7-amino-desacetoxy-cephalosporanic acid which comprises reacting 7-phenoxyacetamido-desacetoxy-cephalosporanic acid with penicillinacylase obtained from *E. coli* bound by covalent bonds to a water-insoluble carrier which comprises tetramethylene glycol dimethacrylate, methacrylic acid and maleic anhydride.

* * * * *